Jan. 24, 1967 R. KORDES Plant Pat. 2,700
ROSE PLANT
Filed Dec. 14, 1965
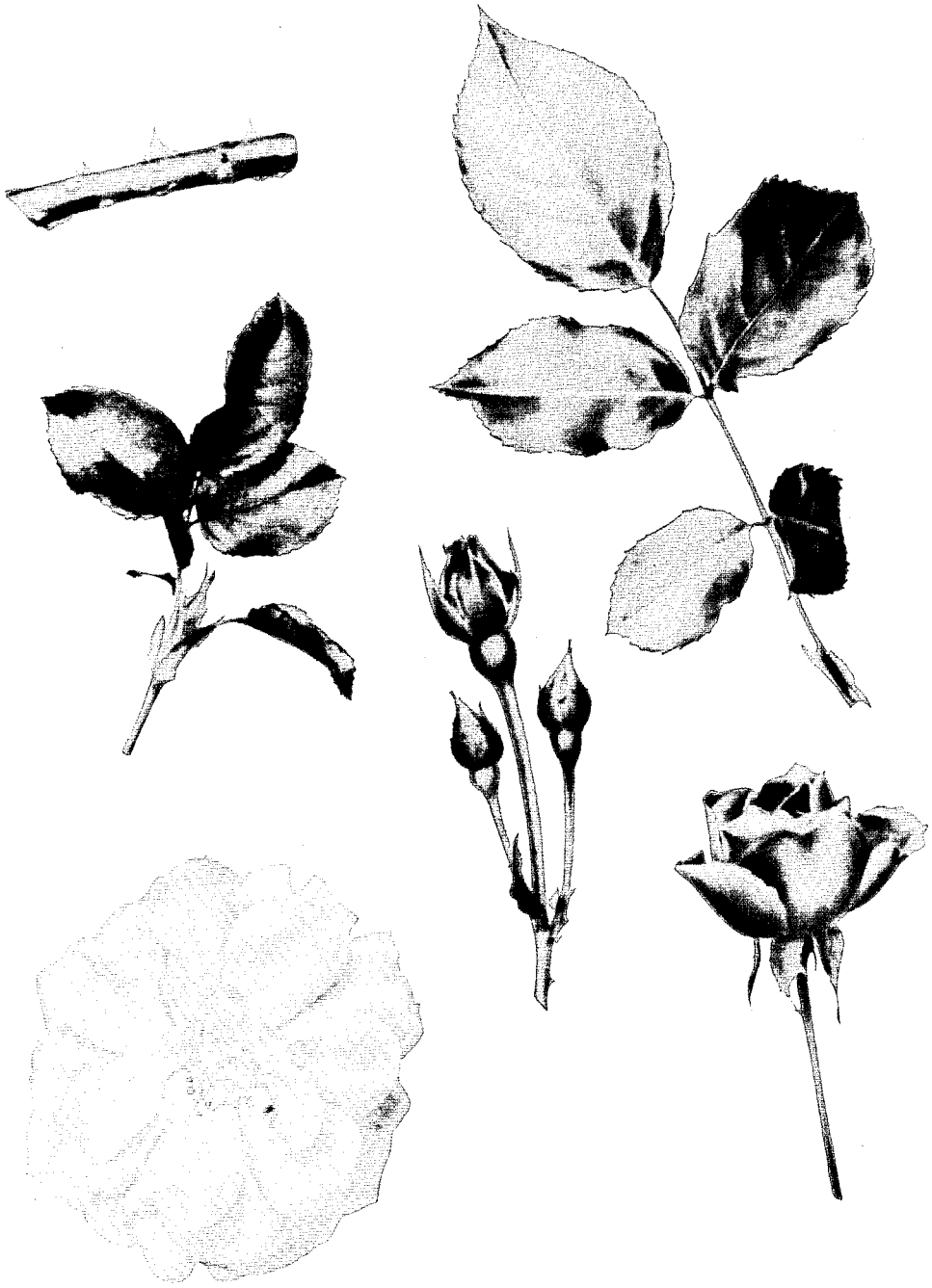
Inventor.
Reimer Kordes
By: Robb & Robb
Attorneys.

United States Patent Office

Plant Pat. 2,700

Patented Jan. 24, 1967

2,700

ROSE PLANT

Reimer Kordes, Barmstedt, near Elmshorn, Germany, assignor to Jackson & Perkins Company, Newark, N.Y., a corporation of New York Filed Dec. 14, 1965, Ser. No. 513,875
1 Claim. (Cl. Plt.—28)

The present invention relates to a new and distinct variety of rose plant of the floribunda class, which was originated by me by crossing the variety known as "Gertrud Westphal" (unpatented) with the variety known as "Lilli Marlene" (U.S. Plant Patent No. 1,986).

The primary objective of this breeding was to produce a new red rose variety of the floribunda type which is an improvement over the parent variety "Lilli Marlene." This objective was fully achieved along with other desirable improvements, as evidenced by the following unique combination of characteristics which are outstanding in the new variety and which distinguish it from its parents, as well as from all other varieties of which I am aware:

(1) A small plant which is about ½ the size of "Lilli Marlene";

(2) A habit of bearing flowers similar to those of "Lilli Marlene," but which are smaller and only about ½ the size of those of this parent variety, thereby resulting in a very low-growing floribunda rose which is suitable for use for either pot forcing or for garden use; and (3) A distinctive and attractive red general color tonality of the flowers.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Gertrud Westphal."
*Pollen parent.*—"Lilli Marlene."
Classification:
*Botanic.*—Floribunda.
*Commercial.*—Floribunda.

*Flower*

(Observations made from specimens grown outdoors at Newark, New York, U.S.A., in the early morning during the latter part of the month of August.)

Blooming habit: Recurrent—continuous.
Bud:
*Size.*—Small.
*Form.*—Ovoid; is not affected by wet or hot weather.
*Color.*—When sepals first divide—Victoria Lake, Plate 1. When petals begin to unfurl—Oxblood Red, Plate 1, very lightly overcast with Carmine, Plate 1. When half-blown: Inside of petals—Bordeaux, Plate 12, lightly overcast with Carmine, Plate 1; reverse of petals—Carmine, Plate 1, lightly overcast with Spectrum Red, Plate 1.
*Sepals.*—Slightly branched; curl back when petals begin to unfurl. Color: Inside—Parrot Green, Plate 6; outside—Oil Green, Plate 5.
*Calyx.*—Color—Lettuce Green, Plate 5. Shape—pear. Size—long. Aspect—smooth. Odor when rubbed—none.
*Peduncle.* — Length — medium. Aspect — smooth. Strength—erect; heavy. Color—Yellowish-Citrine, Plate 16.
*Opening.*—Opens up well; is not affected by adverse weather conditions.
Bloom:
*Size.*—Small. Average size when fully expanded—2½ inches.
*Borne.*—Both singly and several together.
*Stems.*—Medium length; strong.
*Form (when first open).*—From cupped to flat. Permanence—retains its form to the end.
*Petalage.*—Double (full but open center). Number of petals under normal conditions—25.
*Color.*—Center of flower—Nopal Red, Plate 1, very lightly overcast with Spectrum Red, Plate 1. Outer petals—Nopal Red, Plate 1. Base of petals (aiglet)—Deep Rose Pink, Plate 12. Inside of petals—Spectrum Red, Plate 1, lightly overcast with Nopal Red, Plate 1. Reverse of petals—Nopal Red, Plate 1. General tonality from a distance—Spectrum Red, Plate 1, lightly overcast with Nopal Red, Plate 1.
*Discoloration.*—General tonality at end of first day—Nopal Red, Plate 1, overcast with Spectrum Red, Plate 1. Second day—Spectrum Red, Plate 1, lightly overcast with Nopal Red, Plate 1. Third day—Spectrum Red, Plate 1, lightly overcast with Nopal Red, Plate 1.
Petals:
*Texture.*—Thick; is not affected by wet or hot weather.
*Appearance.*—Inside—velvety. Outside—satiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; many; arranged regularly around styles. Color—Deep Chrome, Plate 3.
Stamens, filaments (threads): Short. Color—Flesh-Pink, Plate 13.
Pollen: Color—Cartridge Buff, Plate 30.
Styles: Loosely separated; uneven length; short; thin.
Stigmas: Color—Ivory Yellow, Plate 30.
Ovaries: All enclosed in calyx.
Hips: None.
Seeds: None.

*Plant*

Form: Bush.
Growth: Vigorous; low branching.
Foliage: Compound of 3–5 leaflets.
*Size.*—Medium.
*Quantity.*—Abundant.
*Color.*—New foliage: Upper side—Van Dyke Red, Plate 13; under side—Eugenia Red, Plate 13, lightly overcast with Van Dyke Red, Plate 13. Old foliage: Upper side—Light Bice Green, Plate 17; under side—Biscay Green, Plate 17.
*Shape.*—Oval pointed.
*Texture.*—Upper side—leathery. Under side—smooth.
*Ribs and veins.*—Ordinary.

*Edge.*—Serrated (saw toothed).

*Serration.*—Both double and single; small.

*Leaf stem.*—Color—Olive Lake, Plate 16. Under side—smooth.

*Stipules.*—Short; bearded.

Wood:

*New wood.*—Color—Yellowish-Citrine, Plate 16. Bark—smooth.

*Old wood.*—Color—Parrot Green, Plate 6. Bark—smooth.

Thorns:

*Thorns.*—Quantity: On main stalks from base—ordinary; on laterals from stalk—ordinary. Form—flat base; medium length; some hooked downward and some hooked upward. Color (when young)—Begonia Rose, Plate 1. Position—irregular.

*Prickles.*—Quantity: On main stalks—none; on laterals—none.

*Short needles.*—Quantity: On main stalks—none; on laterals—none.

I claim:

A new and distinct variety of rose plant of the floribunda class, substantially as herein shown and described, characterized particularly as to novelty by the unique combination of a small plant which is about ½ the size of "Lilli Marlene," a habit of bearing flowers similar to those of "Lilli Marlene," but which are smaller and only about ½ the size of those of this parent variety, thereby resulting in a very low-growing floribunda rose which is suitable for use for either pot forcing or for garden use, and a distinctive and attractive red general color tonality of the flowers.

No references cited.

ABRAHAM G. STONE, *Primary Examiner.*

ROBERT E. BAGWILL, *Examiner.*